United States Patent
Ye et al.

(10) Patent No.: US 12,169,933 B2
(45) Date of Patent: Dec. 17, 2024

(54) SEVERITY QUANTIFICATION AND LESION LOCALIZATION METHOD OF INFECTIOUS DISEASE ON CXR USING VISION TRANSFORMER AND APPARATUS THEREFOR

(71) Applicant: Korea Advanced Institute of Science and Technology, Daejeon (KR)

(72) Inventors: JongChul Ye, Daejeon (KR); Sangjoon Park, Daejeon (KR); Gwanghyun Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 335 days.

(21) Appl. No.: 17/704,879

(22) Filed: Mar. 25, 2022

(65) Prior Publication Data
US 2022/0309661 A1    Sep. 29, 2022

(30) Foreign Application Priority Data

Mar. 26, 2021   (KR) .................. 10-2021-0039509
Jun. 1, 2021    (KR) .................. 10-2021-0070757

(51) Int. Cl.
| | |
|---|---|
| *G06T 7/00* | (2017.01) |
| *A61B 6/00* | (2006.01) |
| *G06T 7/10* | (2017.01) |
| *G06T 7/73* | (2017.01) |
| *G06V 10/32* | (2022.01) |
| *G06V 10/764* | (2022.01) |
| *G06V 10/77* | (2022.01) |

(Continued)

(52) U.S. Cl.
CPC .......... *G06T 7/0012* (2013.01); *A61B 6/5217* (2013.01); *G06T 7/10* (2017.01); *G06T 7/73* (2017.01); *G06V 10/32* (2022.01); *G06V 10/764* (2022.01); *G06V 10/7715* (2022.01); *G06V 10/774* (2022.01); *G06V 10/82* (2022.01); *G06T 2207/10116* (2013.01); *G06T 2207/20081* (2013.01); *G06T 2207/20084* (2013.01); *G06T 2207/30061* (2013.01); *G06T 2207/30096* (2013.01)

(58) Field of Classification Search
USPC ........................................ 382/132
See application file for complete search history.

(56) References Cited

U.S. PATENT DOCUMENTS

2021/0192727 A1* 6/2021 Ward .................. G06T 11/20
2022/0036564 A1* 2/2022 Ye .................... G06T 7/0014
(Continued)

FOREIGN PATENT DOCUMENTS

WO    WO-2020179234 A1 *  9/2020

*Primary Examiner* — Jacky X Zheng
(74) *Attorney, Agent, or Firm* — ArentFox Schiff LLP; Joseph M. Maraia; Marlo Schepper Grolnic (57) ABSTRACT

Disclosed is a method and apparatus for quantifying severity of infectious disease based on a vision transformer using a chest X-ray (CXR) image. Here, a method of quantifying severity of infectious disease based on a vision transformer includes receiving an input CXR image; extracting a feature map from the received input CXR image using a pretrained neural network; classifying a lesion in the input CXR image using the vision transformer based on the extracted feature map; and quantifying severity of the input CXR image based on the extracted feature map and the classified lesion.

16 Claims, 9 Drawing Sheets

(51) Int. Cl.
  *G06V 10/774* (2022.01)
  *G06V 10/82* (2022.01)

(56) References Cited

U.S. PATENT DOCUMENTS

2022/0108129 A1\* 4/2022 Lin .................. G06T 11/60
2022/0198254 A1\* 6/2022 Dalli ................ G06N 3/065

\* cited by examiner

(a) D121 + ViT-B/16 (Ours)

(b) DenseNet-121

SEVERITY QUANTIFICATION AND LESION LOCALIZATION METHOD OF INFECTIOUS DISEASE ON CXR USING VISION TRANSFORMER AND APPARATUS THEREFOR

CROSS-REFERENCE TO RELATED APPLICATION

This application claims the priority benefit of Korean Patent Application No. 10-2021-0039509, filed on Mar. 26, 2021 and Korean Patent Application No. 10-2021-0070757, filed on Jun. 1, 2021 in the Korean Intellectual Property Office, the disclosure of which is incorporated herein by reference.

BACKGROUND

1. Field of the Invention

The following description of example embodiments relates to technology for quantifying severity of infectious disease based on a vision transformer using chest X-ray (CXR) image features, and more particularly, to a method and apparatus that may quantify severity of infectious disease, for example, coronavirus disease 2019 (COVID-19), with a vision transformer using CXR image features.

2. Description of the Related Art

The novel coronavirus disease 2019 (COVID-19), caused by sever acute respiratory syndrome coronavirus-2, is an ongoing pandemic resulting in 113,695,296 people infected with 2,526,007 death worldwide as of 1 Mar. 2021. In the face of the unprecedent pandemic by COVID-19, public health care systems have confronted challenges in many aspects including a critical shortage of medical resources, while many health care providers have themselves been infected. Due to highly transmissible and pathologic natures of COVID-19, the early screening of COVID-19 is becoming increasingly important to prevent future spread of disease and to lessen burden of health care systems.

Currently, real-time polymerase chain reaction (RT-PCR) is an optimal standard in COVID-19 confirmation due to high sensitivity and specificity, but it takes severs hours to acquire the results. As many patients with confirmed COVID-19 present radiological findings of pneumonia, radiologic examinations may be useful for fast diagnosis. Although chest computed tomography (CT) has superior sensitivity and specificity for diagnosis of COVID-19, the routine use of CT places a great burden on a heath care system due to its high cost and relatively longer scan time than chest radiograph (CXR). Therefore, there are practical advantages to use the CXR as a primary screening tool under global pandemic. Common CXR findings of COVID-19 include bilateral involvement, peripheral and lower zone dominance of ground glass opacities, and patchy consolidations. Although it has been reported that the sensitivity and specificity of COVID-19 diagnosis with CXR alone is lower than with CT or RT-PCR, the CXR still has potential for fast screening of COVID-19 during the patient triage, determining the priority of patient's care to help a saturated health care system in a pandemic situation.

Accordingly, although proposed are many approaches using deep learning to diagnose COVID-19 with CXR, the approaches suffer from common problems of a limited number of labelled COVID-19 data, which leads to degrading a poor generalization ability. The reliable generalization performance on an unseen and totally different dataset is crucial for real world adoption of a system.

In general, a most common approach to solve this problem is to build an adversarial and robust model with millions of training data. However, due to saturation of health care systems in many countries, it is difficult to construct well-cured datasets containing a large number of labelled COVID-19 cases. Although the previous studies have tried to mitigate the problem by utilizing transfer learning from other large-scale datasets such as ImageNet or by utilizing a weakly-supervised learning method and anomaly detection, the performance of the studies is often suboptimal and does not guarantee an ability to generalize. Also, since COVID-19 usually involves both lung fields with lower zone dominance, the model needs to extract features based on the global manifestation of the disease.

A transformer, which was first introduced in the field of natural language processing (NLP), refers to a deep neural network based on a self-attention mechanism that results in significantly large receptive fields. After achieving astounding results in NLP, it has inspired a vision community to study application programs in computer vision since it enables modeling long-range dependency within images. A vision transformer (ViT) has first showed how the transformer may totally replace standard convolution operations in a deep neural network achieving state-of-the-art (SOTA) performance. However, since training the vision transformer from scratch requires a large amount of data, a hybrid model is proposed by conjugating a convolutional neural network, for example, a ResNet backbone that produces an initial feature embedding. As such, the transformer trained using a feature corpus generated by the ResNet backbone may mainly focus on learning the global attention. Empirical results show that the hybrid model presents a better performance in a small-sized dataset.

Although such preliminary results are promising, there are stilling remaining concerns that the corpus generated by the ResNet may not be an optimal input feature embedding for diagnosis using CXR. Fortunately, there are several publicly available large-scale datasets for CXR classification that was built before the COVID-19 outbreak. Among them, a CheXpert dataset includes labeled abnormal observations including low-level CXR features, for example, opacity, consolidation, edema, etc., useful for diagnosis of infection disease. Also, there are many advanced convolutional neural network (CNN) architectures that may utilize probabilistic class activation map (PCAM) pooling to explicitly leverage the benefit of the class activation map, thereby improving both classification and localization ability for such low-level features.

SUMMARY

Example embodiments provide a method and apparatus that may perform estimation and severity quantification of infectious disease, for example, coronavirus disease 2019 (COVID-19), with a vision transformer using chest X-ray (CXR) image features.

Example embodiments provide a method and apparatus that may quantify severity in an image estimated as COVID-19 by training a model to classify a low-level feature from a prebuilt large-scale public dataset and by acquiring a feature map from the trained model and then combining the same using a vision transformer.

According to an aspect of an example embodiment, there is provided a method of quantifying severity of infectious disease based on a vision transformer, the method including receiving an input chest X-ray (CXR) image; extracting a feature map from the received input CXR image using a pretrained neural network; classifying a lesion in the input CXR image using the vision transformer based on the extracted feature map; and quantifying severity of the input CXR image based on the extracted feature map and the classified lesion.

The extracting of the feature map may include transforming the received input CXR image to a normalized image and then extracting the feature map from the normalized image using the neural network.

The extracting of the feature map may include transforming the input CXR image to the normalized image by normalizing a width, height, and pixel value range of the input CXR image to a predetermined range.

The quantifying may include localizing the lesion based on the extracted feature map and the classified lesion.

The extracting of the feature map may include extracting, from the input CXR image, the feature map that includes low level features of pneumonia, consolidation, lung opacity, pleural effusion, cardiomegaly, edema, atelectasis, pneumothorax, a support device, and no finding.

The classifying of the lesion may include classifying the lesion by combining information included in the feature map and estimating a final diagnosis using classification results of the classified lesion.

The quantifying may include quantifying the severity of the input CXR image based on a combination of information included in the extracted feature map and the classified lesion and localizing a position of the lesion.

The quantifying may include generating a lesion probability map based on the extracted feature map and the classified lesion and quantifying severity of the input CXR image using the generated lesion probability map.

The quantifying may include segmenting each of a left lung field and a right lung field of the input CXR image into three areas, assigning a maximum lesion probabilistic value to each of the segmented areas, and quantifying the severity of the input CXR image with respect to each of the segmented areas using the assigned maximum lesion probabilistic value.

The neural network may be pretrained by a large-scale labeled first training dataset and then trained by supervised and weakly supervised learning with the vision transformer through training a small-scale labeled second training dataset with respect to the lesion to be classified.

According to another aspect of an example embodiment, there is provided a method of quantifying severity of infectious disease based on a vision transformer, the method including transforming an input chest X-ray (CXR) image to a normalized image; extracting a feature map from the transformed normalized image using a pretrained neural network; classifying a lesion in the input CXR image using the vision transformer based on the extracted feature map; and quantifying severity of the input CXR image based on the extracted feature map and the classified lesion.

According to another aspect of an example embodiment, there is provided an apparatus for quantifying severity of infectious disease based on a vision transformer, the apparatus including a receiver configured to receive an input chest X-ray (CXR) image; an extractor configured to extract a feature map from the received input CXR image using a pretrained neural network; a classifier configured to classify a lesion in the input CXR image using the vision transformer based on the extracted feature map; and a quantifier configured to quantify severity of the input CXR image based on the extracted feature map and the classified lesion.

The extractor may be configured to transform the received input CXR image to a normalized image and then extract the feature map from the normalized image using the neural network.

The extractor may be configured to transform the input CXR image to the normalized image by normalizing a width, height, and pixel value range of the input CXR image to a predetermined range.

The quantifier may be configured to localize the lesion based on the extracted feature map and the classified lesion.

The extractor may be configured to extract, from the input CXR image, the feature map that includes low level features of pneumonia, consolidation, lung opacity, pleural effusion, cardiomegaly, edema, atelectasis, pneumothorax, a support device, and no finding.

The classifier may be configured to classify the lesion by combining information included in the feature map and to estimate a final diagnosis using classification results of the classified lesion.

The quantifier may be configured to quantify the severity of the input CXR image based on a combination of information included in the extracted feature map and the classified lesion and to localize a position of the lesion.

The quantifier may be configured to generate a lesion probability map based on the extracted feature map and the classified lesion and to quantify severity of the input CXR image using the generated lesion probability map.

The quantifier may be configured to segment each of a left lung field and a right lung field of the input CXR image into three areas, to assign a maximum lesion probabilistic value to each of the segmented areas, and to quantify the severity of the input CXR image with respect to each of the segmented areas using the assigned maximum lesion probabilistic value.

The neural network may be pretrained by a large-scale labeled first training dataset and then trained by supervised and weakly supervised learning with the vision transformer through training a small-scale labeled second training dataset with respect to the lesion to be classified.

According to some example embodiments, it is possible to perform estimation and severity quantification of infectious disease, for example, COVID-19, with a vision transformer using CXR image features. Here, by training a model to classify a low-level feature in a dataset and by acquiring a feature map from the trained model and then combining the same using the vision transformer, it is possible to quantify severity in an image diagnosed with COVID-19.

According to some example embodiments, since it is possible to perform severity quantification as well as estimation, it is possible to minimize spread of infectious disease and to induce efficient distribution of medical resources in an infectious disease screening and treatment process and also to effectively assist a clinical doctor in the process of verifying and following up the treatment effect. For example, by quantifying severity of a patient diagnosed with infectious disease, for example, COVID-19, using a simple CXR image, it may be usefully used even in a follow-up and treatment plan process of the diagnosed patient.

According to some example embodiments, since a low-level feature is extracted using a model trained from a large-scale dataset, generalization performance degradation barely occurs. Also, since final results are acquired by combining low-level features using the vision transformer trained with small-scale labeled data, it is less affected by generalization performance degradation.

CXR imaging may apply not only in the medical market but also in private facilities lacking specialized medical personnel since an imaging method is simpler and faster than other infectious disease diagnosis technology. If the present disclosure is used as an infectious disease screening treatment in an environment in which the population is dense and specialized medical resources are lacking, such as an airport, a military facility, and a developing country, it is possible to effectively prevent reckless spread of infectious disease.

Further regions of applicability will become apparent from the description provided herein. The description and specific examples in this summary are intended for purposes of illustration only and are not intended to limit the scope of the present disclosure.

BRIEF DESCRIPTION OF THE DRAWINGS

These and/or other aspects, features, and advantages of the disclosure will become apparent and more readily appreciated from the following description of embodiments, taken in conjunction with the accompanying drawings of which.

DETAILED DESCRIPTION

Advantages and features of the present disclosure and a method for achieving the same will be described in detail with reference to the accompanying drawings and the following example embodiments. However, the present disclosure is not limited to the following example embodiments disclosed herein and may be implemented in various different forms. Here, the example embodiments are provided such that the present disclosure is complete and to completely inform one of ordinary skill in the art to which the present disclosure pertains and the present disclosure may be defined by the scope of the claims.

The terms used herein is for describing various example embodiments only, and is not construed to limit the present disclosure. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Hereinafter, the example embodiments are described in detail with reference to the accompanying drawings. Like reference numerals refer to like components throughout, wherever possible, even though they are shown in different drawings. Further description related thereto is omitted.

Severity quantification of coronavirus disease 2019 (COVID-19) and lesion localization with respect to chest X-ray (CXR) may be usefully used even in a follow-up and treatment plan process of a diagnosed patient. To quantify and localize the severity based on deep learning, pixel-level labelling is usually useful, but a large amount of time and efforts is required to construct a dataset including such a label. Therefore, introduced is an array-based labeling scheme that segments a chest into six areas and assigns 1 or 0 to each of the six areas depending on whether a lesion related to COVID-19 is present. Proposed is a deep learning-based approach that quantifies severity of COVID-19 and localizes a lesion based on a dataset constructed using this labelling.

To develop technology for an infectious disease diagnosis artificial neural network using simple chest X-ray (CXR) image, large-scale learning data is essential. The more learning is performed using single institution data that has undergone a consistent preprocessing process, the higher performance, such as accuracy and sensitivity. However, in a situation in which infectious disease is globally pandemic, there is a limit in constructing a consistently refined multi-institutional dataset. Therefore, although a process of learning using pre-constructed datasets or datasets acquired from various sources in reality is required, training an artificial neural network in this manner may rapidly degrade performance in a new dataset and achieve performance only in a dataset used for learning. That is, generalization performance and overfitting issues may arise.

Example embodiments relate to quantifying severity in an image estimated or diagnosed with infectious disease, for example, COVID-19 by training a model to classify a low-level feature in a prebuilt large-scale public dataset and by acquiring a feature map from the trained model and then combining the same using a vision transformer.

Herein, since a low-level feature is extracted using the model trained from a large-scale dataset, generalization performance degradation barely occurs. Also, since final results are acquired by combining low-level features using the vision transformer trained with small-scale labeled data, it is less affected by generalization performance degradation. That is, the example embodiments may outperform the general performance degradation in small-scale learning data and may predict a severity map using a weakly-supervised learning model from a label of a severity array that may be collected in a short time with little labor and may improve prediction accuracy of the severity map through a weakly-supervised learning method from the label of the simple severity array.

Figure 1:
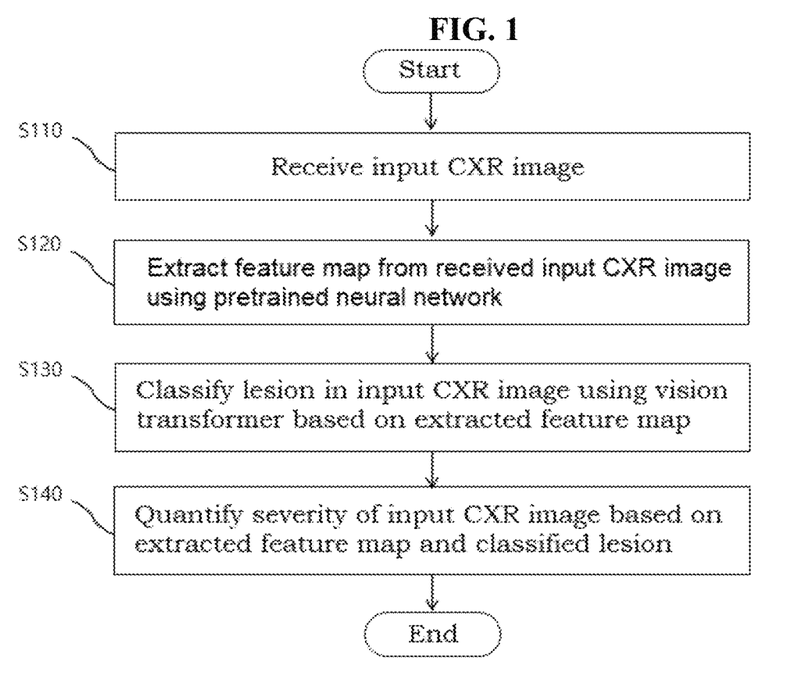
FIG. 1 is a flowchart illustrating a method of quantifying severity of infectious disease based on a vision transformer according to an example embodiment.

FIG. 1 is a flowchart illustrating a method of quantifying severity of infectious disease based on a vision transformer according to an example embodiment.

Referring to FIG. 1, a method of quantifying severity of infectious disease based on a vision transformer according to an example embodiment includes operation S110 of receiving an input CXR image, operation S120 of extracting a feature map from the received input CXR image using a pretrained neural network, operation S130 of classifying a lesion in the input CXR image using the vision transformer based on the extracted feature map, and operation S140 of quantifying severity of the lesion, for example, COVID-19 based on the extracted feature map and the classified lesion.

In operation S110, the method may receive an image diagnosed with infectious disease, for example, a CXR image diagnosed with COVID-19, or may receive a CXR image to determine presence or absence of the infectious disease.

In operation S120, the method may transform the received input CXR image to a normalized image and then extract the feature map from the normalized image using the neural network in operation S110, for example, a backbone network or a feature embedding network.

Here, in operation S120, the method may transform the input CXR image to the normalized image by normalizing a width, height, and pixel value range of the input CXR image to a predetermined range. The method of the present disclosure may omit a process of transforming the input CXR image to the normalized image if necessary, which may be determined by a provider or an individual that provides the art of the present disclosure.

The neural network in operation S120 may be pretrained by a large-scale labeled first training dataset and then trained by supervised and weakly supervised learning with the vision transformer through training a small-scale labeled second training dataset with respect to the lesion to be classified, for example, COVID-19. In this manner, the neural network may extract a feature map for the lesion to be classified from the input CXR image.

Here, in operation S120, the method may extract, from the input CXR image, the feature map that includes low level features of pneumonia, consolidation, lung opacity, pleural effusion, cardiomegaly, edema, atelectasis, pneumothorax, a support device, and no finding.

In operation S130, the method may classify the lesion by combining information included in the feature map and may estimate a final diagnosis using classification results of the classified lesion, or may classify a most classified lesion among lesion classification results as a final lesion. That is, the vision transformer may generate a final feature to be provided as a map head using the input feature map.

In operation S140, the method may quantify the lesion and localize the lesion based on the lesion classified through the extracted feature map and the vision transformer.

Here, in operation S140, the method may quantify the severity of the input CXR image based on a combination of information included in the extracted feature map and the classified lesion and may localize a position of the lesion.

For example, in operation S140, the method may generate a lesion probability map based on the extracted feature map and the classified lesion and may quantify severity of the input CXR image using the generated lesion probability map, and, here, may segment each of a left lung field and a right lung field of the input CXR image into three areas, may assign a maximum lesion probabilistic value to each of the segmented areas, and may quantify the severity of the input CXR image with respect to each of the segmented areas using the assigned maximum lesion probabilistic value.

The method according to example embodiments is described with reference to FIGS. 2 to 5.

The model of the present disclosure is trained based on anterior CXR images with an annotated severity score array. In particular, each of a left lung and a right lung is segmented into three areas in a vertical direction. A lower portion extends from an intercostal groove to a lower hilar mark, and an intermediate portion extends from the lower hilar mark to an upper hilar mark, and an upper portion runs from the upper hilar mark to the upper hilar mark. Next, each area is segmented into two areas along a horizontal direction across spines. A binary score 0/1 is assigned to each area depending on whether opacity is present. Therefore, a completed label may have an array format of 3×2 and a global severity score that is a sum of all elements in the range of 0 to 6.

Figure 2A:
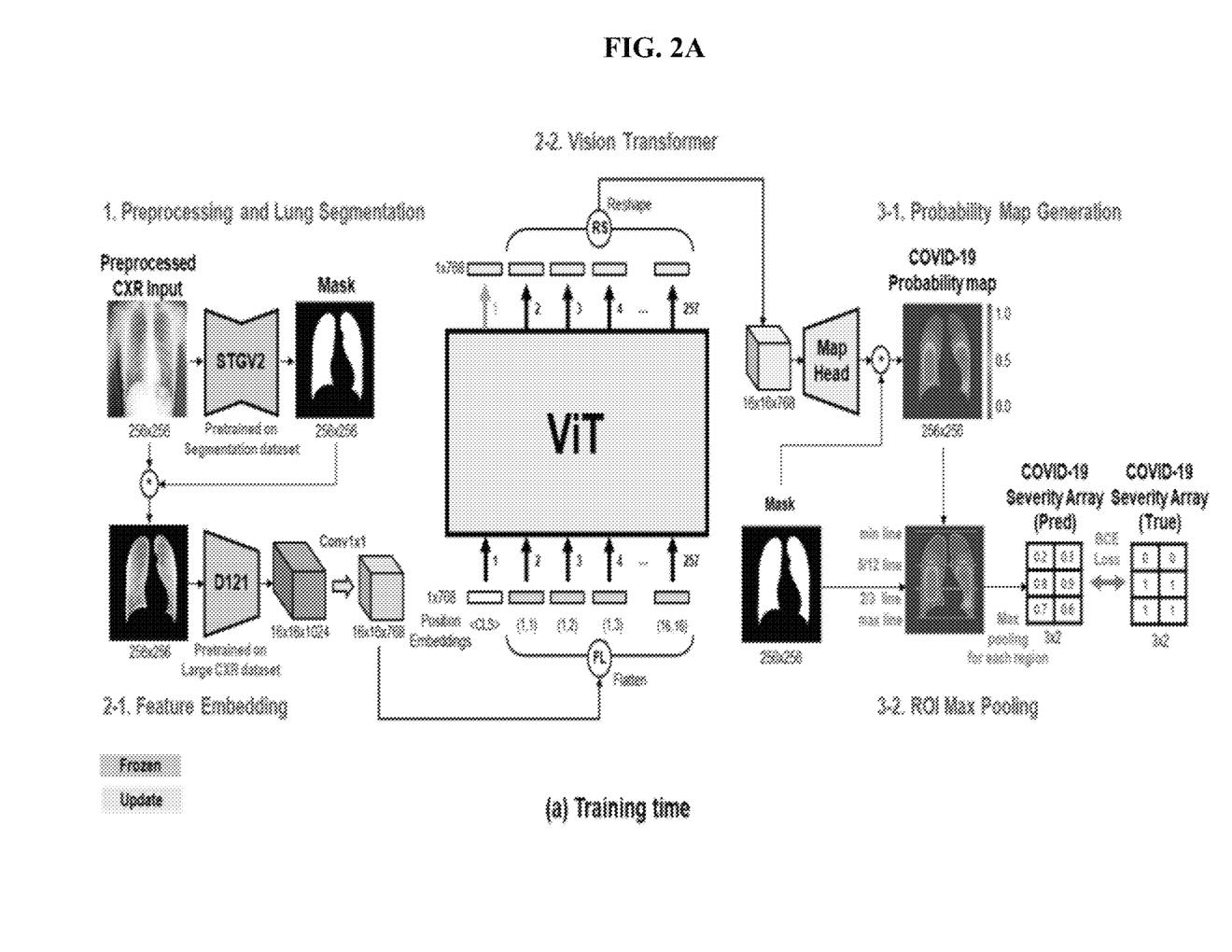
FIGS. 2A, 2B, and 2C illustrate examples of a framework for a method according to an example embodiment.
Figure 2B:
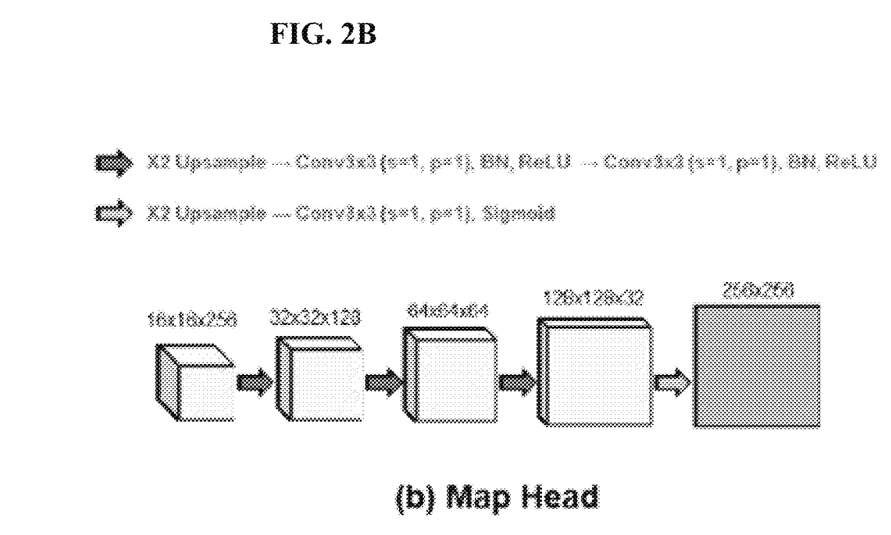
Figure 2C:
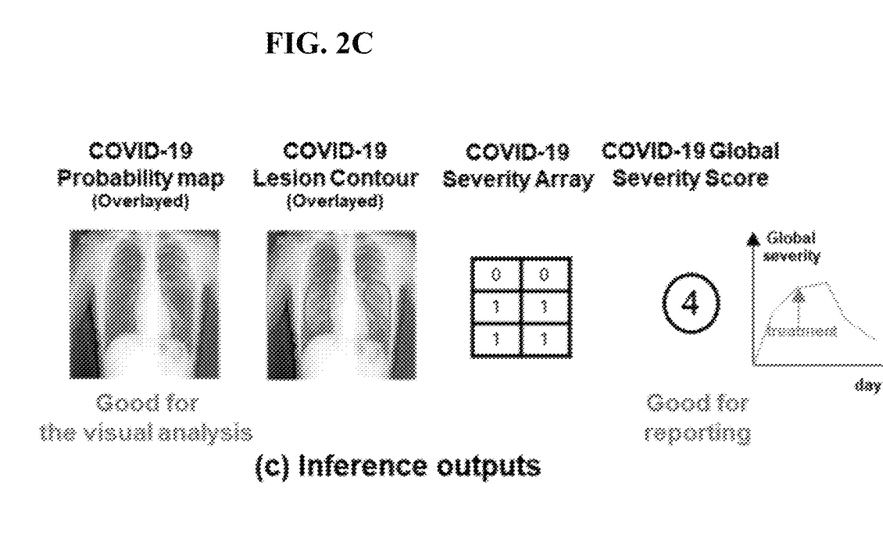

Referring to FIG. 2A, in an overall architecture of the model of the present disclosure, an input CXR image is preprocessed and is assigned to a lung segmentation network (STGV2). A segmented lung image is supplied to a feature embedding network and leads to a vision transformer (ViT). Referring to FIG. 2B, a final feature generated by the vision transformer is provided to a map head that generates a complete COVID-19 probability map. Referring to FIG. 2C, 3×2 COVID-19 severity array is estimated as a final output through ROI max pooling.

The merit of the model of the present disclosure is that the transformer may exploit a low-level CXR feature corpus acquired through a feature embedding network trained to extract an abnormal CXR feature from a publicly available large and well-curated CXR dataset.

Figure 3A:
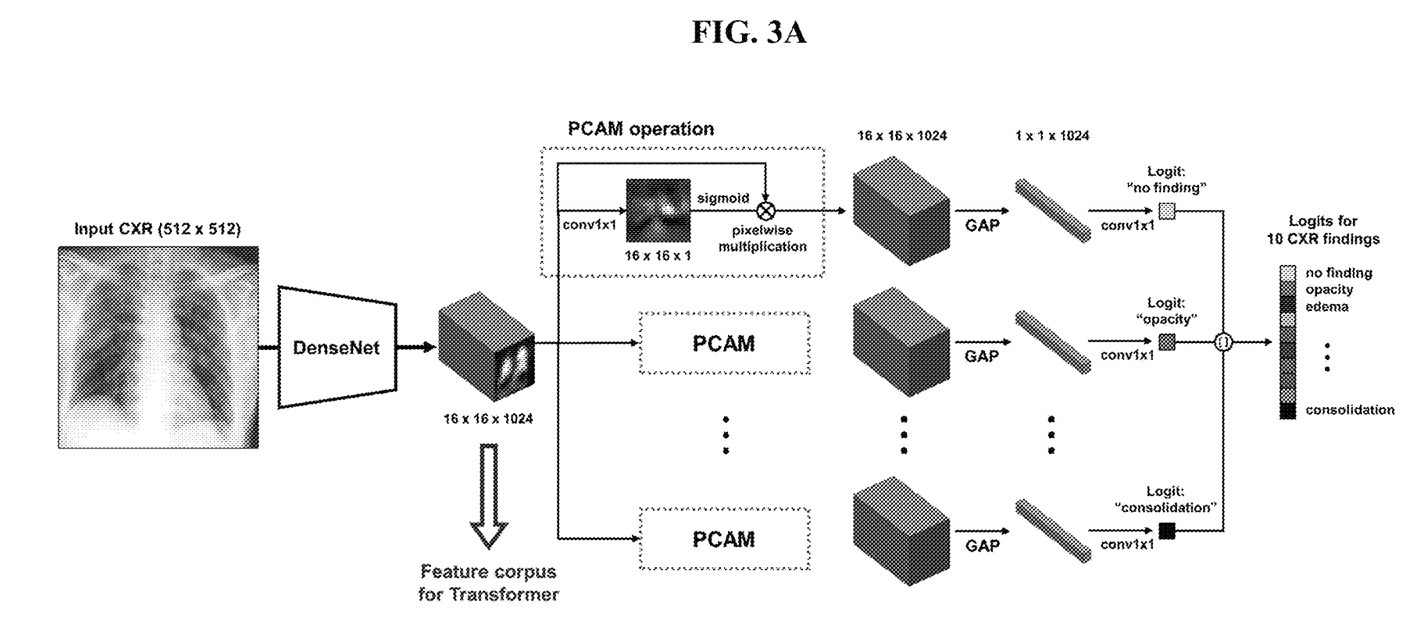
FIGS. 3A and 3B illustrate examples of a structure of a feature embedding network and a structure of a vision transformer.

Pretraining a feature embedding network for a low-level feature corpus: Referring to FIG. 3A, as a feature embedding network (or a backbone network) to extract a low-level-CXR feature corpus in an image, the model utilizes a probabilistic class activation map (PCAM) pooling for output of a DenseNet-121-bsed feature extractor to explicitly leverage the benefit of a class activation map to improve both classification and localization ability. The feature embedding network may be pretrained with a prebuilt public CXR image dataset to classify 10 labelled observations including pneumonia, consolidation, lung opacity, pleural effusion, cardiomegaly, edema, atelectasis, pneumothorax, support device, and no finding. In detail, the present disclosure may use 16×16×1024 features before transform layer 3 of DenseNet-121

Referring to FIG. 3A, the feature embedding network or the backbone network may include a plurality of layers that may extract a feature embedding and an intermediate level embedding before a PCAM operation includes most useful information. However, attention needs to be paid since a PCAM apparatus trained with a specific low-level CXR feature, e.g., cardiomegaly, lung opacity, edema, and consolidation, is essential to improve accuracy of the intermediate level feature embedding by guiding the feature aligned to provide an optimal PCAM map. Specifically, with a pretrained feature embedding network F, an input image, for example, a segmented lung $x \in \mathbb{R}^{H \times W \times C}$ may be encoded (or projected) into an intermediate feature map $c \in \mathbb{R}^{H' \times W' \times C'}$. $C'$ dimensional feature vector $c$ of each of $H' \times W'$ pixels may be used as encoded representation for a low-level feature at each pixel position and may construct a low-level CXR feature corpus, which may be represented as the following Equation 1 and Equation 2.

$$c = F(x), x \in \mathbb{R}^{H \times W \times C}, c \in \mathbb{R}^{H' \times W' \times C'} \qquad \text{[Equation 1]}$$

$$c = [c^1; c^2; c^3; \ldots ; c^{H' \times W'}], c \in \mathbb{R}^{C'} \qquad \text{[Equation 2]}$$

Figure 3B:
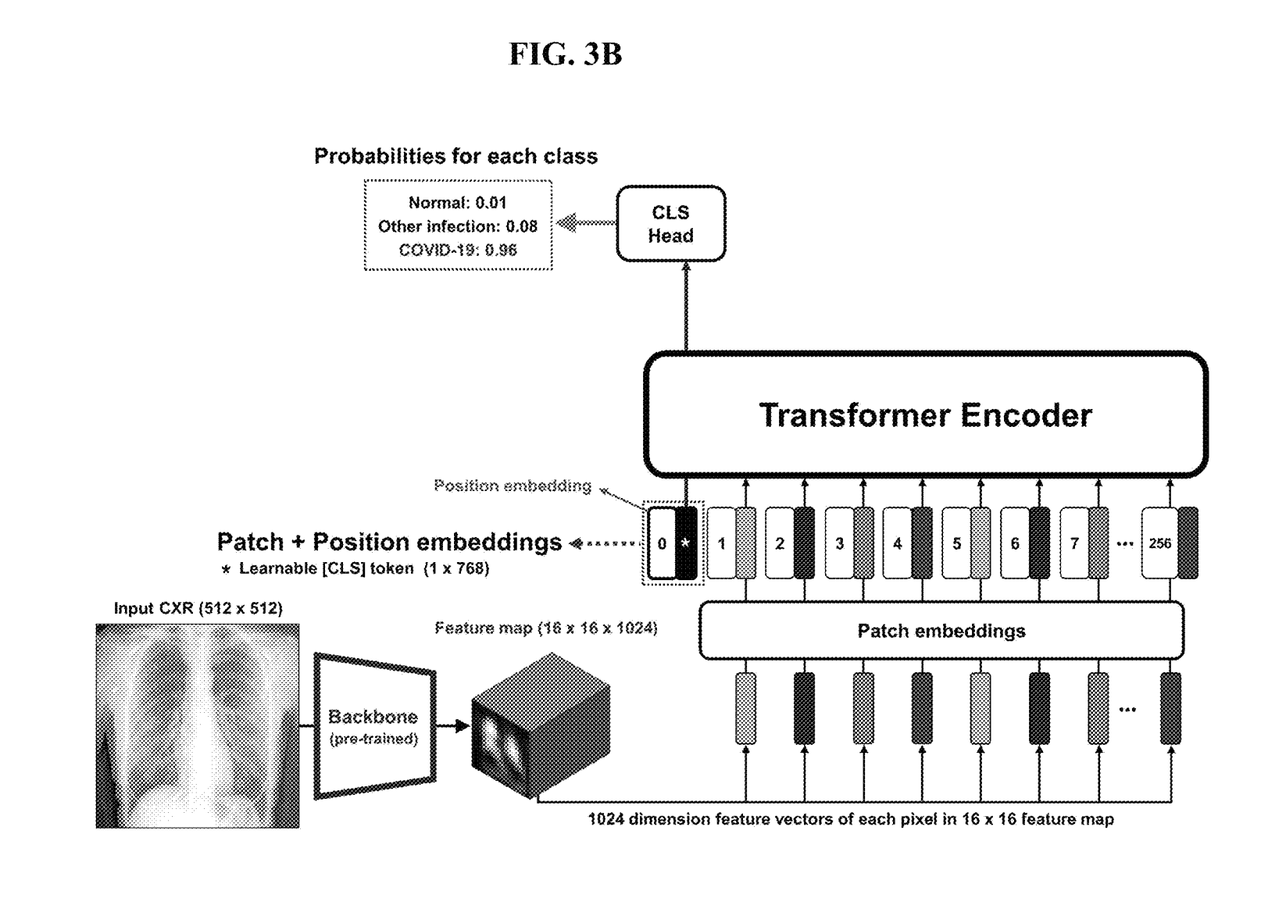

Vision transformer: Referring to FIG. 3B, similar to BERT (Devlin, J., Chang, M. W., Lee, K., Toutanova, K.:

Bert: Pretraining of deep bidirectional transformers for language understanding. arXiv preprint arXiv:1810.04805 (2018)), as an encoder-only architecture, a vision transformer model adopts ViT-B/16 architecture and an input may be 16×16 patches. A transformer encoder projects an encoded feature c of dimension C' into $c_p$ of dimension D using a 1×1 convolution kernel. Similar to [class] token of BERT, the present disclosure may prepend an additional learnable embedding vector $c_{cls}$ to the projected feature $c_p$ to make a last L layer output of [class] token $z^0_L$ represent a diagnosis of the entire CXR image (=y) by attaching a classification head to $z^0_L$. The learnable vector $c_{cls}$ that is a role of [class] token of BERT is included in ViT training. However, a final layer output of ViT-B/16 is used except for output of a token position. Also, the present disclosure may add a positional embedding $E_{pos}$ to encode a notion of sequential order to the projected feature $c_p$. In this manner, position information of the feature map is not lost. A transformer encoder layer used in the model disclosed herein is the same as a standard transformer encoder that includes alternating layers of a multihead self-attention (MSA), multilayer perceptron (MLP), layer normalization (LN), and residual connection in each block, which may be represented as the following Equation 3.

$$[c_p^1; c_p^2; c_p^3; \ldots; c_p^{H' \times W'}] = \mathrm{conv}([c^1; c^2; c^3; \ldots; c^{H' \times W'}]), c_p \in \mathbb{R}^D$$

$$[z_0^0; z_0^1; z_0^2; \ldots; z_0^{H' \times W'}] = [c_{cls}; c_0^1 c_p^2; c_p^3; \ldots; c_p^{H \times W'}] + E_{pos}$$

$$z_0 = [z_0^0; z_0^1; z_0^2; \ldots; z_0^{H' \times W'}]$$

$$z'_l = \mathrm{MSA}(\mathrm{LN}(z_{l-1})) + z_{l-1}, l = 1 \ldots L$$

$$z_l = \mathrm{MLP}(\mathrm{LN}(z'_l)) + z'_l, l = 1 \ldots L$$

In Equation 3, L denotes a number of layers of ViT. For example, in the case of ViT-B/16, L may be 12.

Probability map generation and ROI max pooling: A map head using output of ViT includes four upsizing convolution blocks and generates a map with the same size as an input size. FIG. 2B illustrates a detailed structure of the map head. By multiplying the output of the map head by lung mask $m \in \mathbb{R}^{H \times W}$, COVID-19 lesion probability map $y \in \mathbb{R}^{H \times W}$ is generated. Referring to FIG. 2A, ROI max-pooling (RMP) may be used to transform COVID-19 lesion map to severity array $a \in \mathbb{R}^{3 \times 2}$, and the lesion probability map and the severity array may be represented as the following Equation 4.

$$y = \mathrm{MAPHEAD}([z_L^1; z_L^2; z_L^3; \ldots; z_L^{H' \times W'}]) \otimes m, y, m \in \mathbb{R}^{H \times W}$$

$$a = \mathrm{RMP}(y, m), a \in \mathbb{R}^{3 \times 2}$$

In particular, the lung is segmented into a right lung and a left lung by computing a component connected to a lung mask. Next, each of the left lung and the right lung is segmented into three areas by segmentation lines at 5/12 and 2/3 points of a highest position and a lowest position of the lung mask. A maximum value of each of the six areas is assigned to each corresponding element of 3×2 array. To optimize the model, a binary cross-entropy loss between the predicted severity array and the label severity array is computed. This line estimation and max pooling process may be a key to a weakly supervised learning plan.

Self-Training for an Unlabeled Dataset

In a pandemic situation, it is often difficult to collect sufficient severity labels even though a labeling method is very simple. The present disclosure may employ self-training that uses a large unlabeled severity dataset and a small labeled severity dataset capable of improving performance of the model. A detailed process of a self-training method is shown in FIG. 4.

Figure 4:
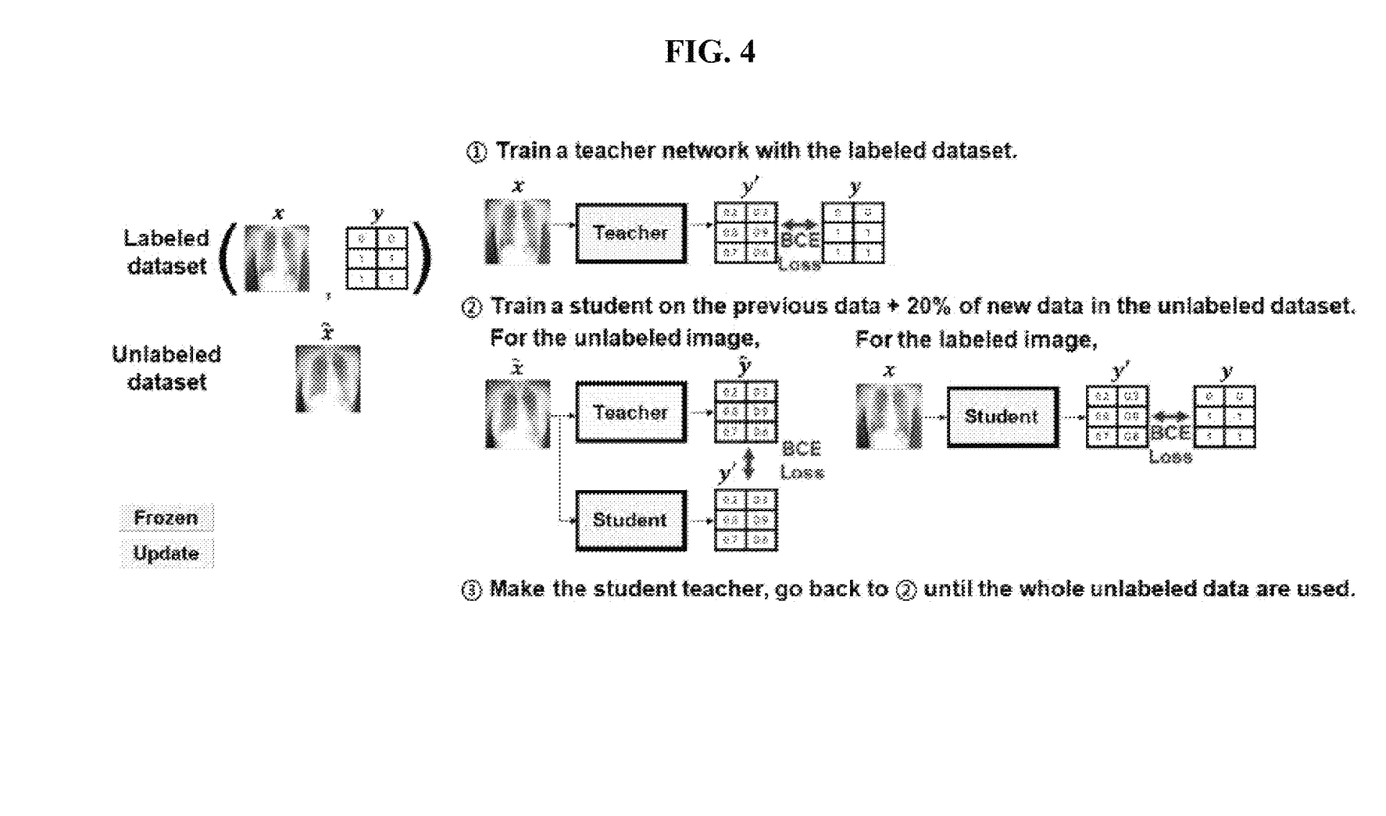
FIG. 4 illustrates an example of a self-training method.

Describing the self-training method with reference to FIG. 4, in a first stage, a teacher network is trained with a labeled dataset. In a second stage, a student network generated with a copy of a new teacher is trained with a dataset in which a portion of a new unlabeled dataset is added to a previous dataset. The student model is optimized with a pseudo label generated by the teacher network with respect to an input unlabeled by a true label for a labeled input. Next, a student becomes a new teacher and, by returning to the second stage, the process is repeated and the student model is continuously updated.

The following Table 1 shows a quantitative comparison of severity quantification performance for an external dataset of Chonnam National University Hospital (CNUH). Referring to Table 1, it can be seen that the model of the present disclosure shows excellent performance and generalization probability than a CNN-based model in many metrics. Here, MSE denotes a mean square error and may be used as a main metric for regression of global severity score range of 0 to 6, MAE denotes a mean absolute error, CC denotes a correlation coefficient, $R^2$ denotes a score for a global score regression, and AUC denotes an area average under ROC curve.

TABLE 1

| Backbone | Params (M) | MSE | MAE | CC | $R^2$ | Mean AUC |
|---|---|---|---|---|---|---|
| D121 + ViT-B/16 | 95.5 | 1.889 | 0.926 | 0.760 | 0.520 | 0.882 |
| ResNet-18 | 3.4 | 2.012 | 0.975 | 0.735 | 0.488 | 0.875 |
| DenseNet-121 | 13.6 | 2.000 | 0.914 | 0.730 | 0.491 | 0.873 |
| DenseNet-201 | 38.0 | 2.395 | 1.086 | 0.676 | 0.391 | 0.849 |
| ResNet-152 | 52.5 | 2.235 | 0.951 | 0.716 | 0.432 | 0.356 |
| NASNet-Large | 56.1 | 2.592 | 0.963 | 0.715 | 0.311 | 0.073 |

Figure 5:
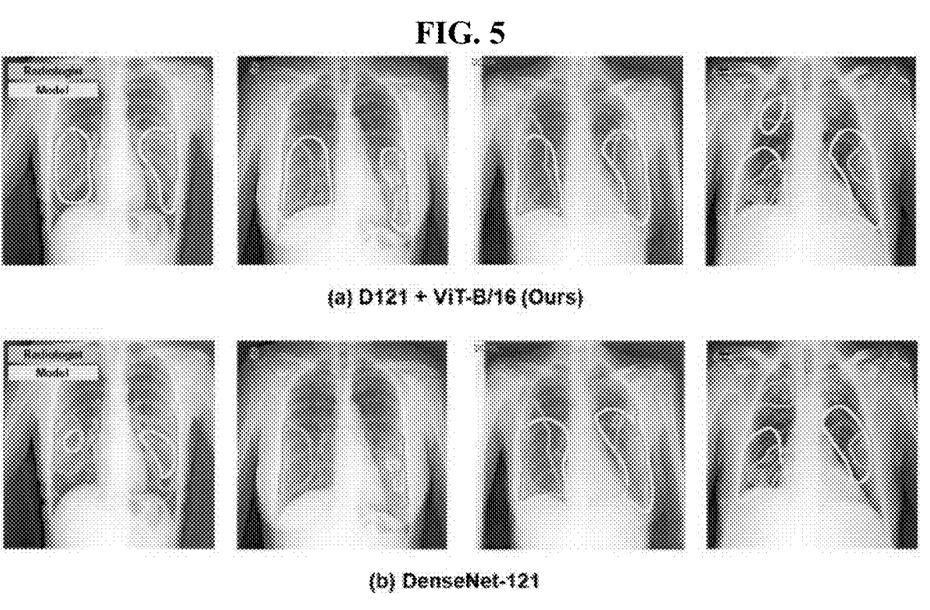
FIG. 5 illustrates an example of comparing localization performance for BIMCV external dataset between a model for a method according to an example embodiment and a DenseNet-121-based model.

FIG. 5 illustrates an example of comparing localization performance for BIMCV external dataset between a model for a method according to an example embodiment and a DenseNet-121-based model. Referring to FIG. 5, it can be seen that prediction of an abnormal area in a CXR image of a model (a) of the present disclosure shows a more accurate localization than a DenseNet-121-based model (b).

The method according to example embodiments may perform estimation and severity quantification of infectious disease, for example, COVID-19 with a vision transformer using a CXR image feature and, here, may quantify the severity in an image estimated or diagnosed with infectious disease, for example, COVID-19 by training a model to classify a low-level feature in a prebuilt large-scale public dataset and by acquiring a feature map from the trained model and then combining the same using the vision transformer.

Also, the method according to example embodiments, since it is possible to perform severity quantification as well as estimation, it is possible to minimize spread of infectious disease and to induce efficient distribution of medical resources in an infectious disease screening and treatment process and also to effectively assist a clinical doctor in the process of verifying and following up the treatment effect. For example, by quantifying severity of a patient diagnosed with an infectious disease, for example, COVID-19 using a simple CXR image, it may be usefully used even in a follow-up and treatment plan process of the diagnosed patient.

Also, in the method according to example embodiments, since a low-level feature is extracted using a model trained from a large-scale dataset, generalization performance degradation barely occurs. Also, since final results are acquired by combining low-level features using the vision transformer trained with small-scale labeled data, it is less affected by generalization performance degradation.

Also, the method according to example embodiments may be employed for any type of algorithms for deriving high-level result values by combining low-level features without being limited to quantification and diagnosis of infectious diagnosis and may develop a severity quantification model showing performance of a clinical expert level from a severity-unlabeled dataset and a small-scale severity labeled dataset using self-training.

In the method according to example embodiments, one of the most important advantages of a new virtual transformer system for severity quantification and lesion localization may lead a global attention map of a transformer to a global lesion map. Here, each pixel value may directly represent abnormality probabilities of COVID-19 and self-training may use a large severity unlabeled dataset as well as a small severity labeled dataset.

Figure 6:
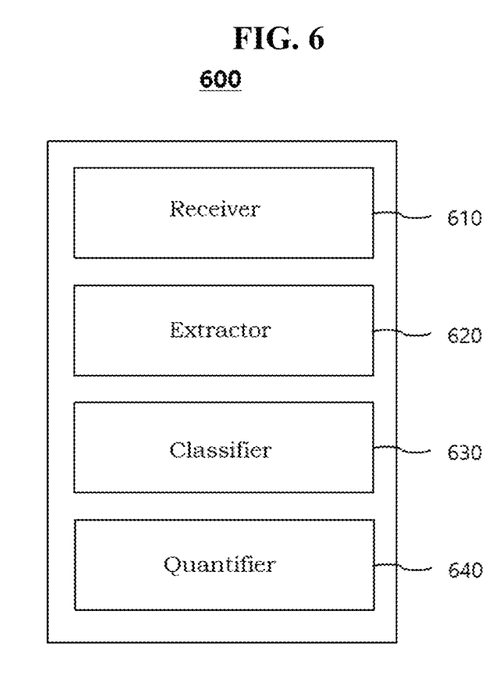
FIG. 6 is a diagram illustrating a configuration of an apparatus for quantifying severity of infectious disease based on a vision transformer according to an example embodiment.

FIG. 6 is a diagram illustrating a configuration of an apparatus for quantifying severity of infectious disease based on a vision transformer according to an example embodiment and illustrates a conceptual configuration of an apparatus that performs the method of FIGS. 1 to 5.

Referring to FIG. 6, an apparatus 600 for quantifying severity of infectious disease based on a vision transformer according to an example embodiment includes a receiver 610, an extractor 620, a classifier 630, and a quantifier 640.

The receiver 610 receives an input CXR image.

Here, the receiver 610 may receive an image diagnosed with an infectious disease, for example, a CXR image diagnosed with COVID-19, or may receive a CXR image to determine presence or absence of an infectious disease.

The extractor 620 extracts a feature map from the received input CXR image using a pretrained neural network.

Here, the extractor 620 may transform the received input CXR image to a normalized image and then extract the feature map from the normalized image using the neural network.

The extractor 620 may transform the input CXR image to the normalized image by normalizing a width, height, and pixel value range of the input CXR image to a predetermined range.

The neural network in the extractor 620 may be pretrained by a large-scale labeled first training dataset and then trained by supervised and weakly supervised learning with the vision transformer through training a small-scale labeled second training dataset with respect to the lesion to be classified, for example, COVID-19. In this manner, the neural network may extract a feature map for the lesion to be classified from the input CXR image.

Here, the extractor 620 may extract, from the input CXR image, the feature map that includes low level features of pneumonia, consolidation, lung opacity, pleural effusion, cardiomegaly, edema, atelectasis, pneumothorax, a support device, and no finding.

The classifier 630 classifies the lesion in the input CXR image using the vision transformer based on the extracted feature map.

Here, the classifier 630 may classify the lesion by combining information included in the feature map and may estimate a final diagnosis using classification results of the classified lesion, or may classify a most classified lesion among lesion classification results as a final lesion. That is, the vision transformer may generate a final feature to be provided as a map head using the input feature map.

The quantifier 640 quantifies severity of the lesion, for example, COVID-19 based on the extracted feature map and the classified lesion.

Also, the quantifier 640 may quantify the lesion and localize the lesion based on the lesion classified through the extracted feature map and the vision transformer.

Here, the quantifier 640 may quantify the severity of the input CXR image based on a combination of information included in the extracted feature map and the classified lesion and may localize a position of the lesion.

For example, the quantifier 640 may generate a lesion probability map based on the extracted feature map and the classified lesion and may quantify the severity of the input CXR image using the generated lesion probability map, and, here, may segment each of a left lung field and a right lung field of the input CXR image into three areas, may assign a maximum lesion probabilistic value to each of the segmented areas, and may quantify the severity of the input CXR image with respect to each of the segmented areas using the assigned maximum lesion probabilistic value.

Although corresponding description is omitted in the apparatus of FIG. 6, it will be apparent to those skilled in the art that description made above with reference to FIGS. 1 to 5 may apply to each component of FIG. 6.

The apparatuses described herein may be implemented using hardware components, software components, and/or a combination of hardware components and software components. For example, a processing device and components described herein may be implemented using one or more general-purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and/or data may be embodied permanently or temporarily in any type of machine, component, physical equipment, virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable storage mediums.

The methods according to the example embodiments may be recorded in non-transitory computer-readable media including program instructions to implement various operations embodied by a computer. Also, the media may include, alone or in combination with the program instructions, data files, data structures, and the like. Program instructions stored in the media may be those specially designed and constructed for the purposes, or they may be of the kind well-known and available to those having skill in the computer software arts. Examples of non-transitory computer-readable media include magnetic media such as hard disks, floppy disks, and magnetic tape; optical media such as CD ROM disks and DVD; magneto-optical media such as floptical disks; and hardware devices that are specially to store and perform program instructions, such as read-only memory (ROM), random access memory (RAM), flash memory, and the like. Examples of other media may include recording media and storage media managed by an app store that distributes applications or a site, a server, and the like that supplies and distributes other various types of software. Examples of program instructions include both machine code, such as produced by a compiler, and files containing higher level code that may be executed by the computer using an interpreter.

While this disclosure includes specific example embodiments, it will be apparent to one of ordinary skill in the art that various alterations and modifications in form and details may be made in these example embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of quantifying severity of infectious disease based on a vision transformer, the method comprising:
    receiving an input chest X-ray (CXR) image;
    extracting a feature map from the received input CXR image using a pretrained neural network;
    classifying a lesion in the input CXR image using the vision transformer based on the extracted feature map; and
    quantifying severity of the input CXR image based on the extracted feature map and the classified lesion,
    wherein the quantifying comprises quantifying the severity of the input CXR image based on a combination of information included in the extracted feature map and the classified lesion and localizing a position of the lesion.

2. The method of claim 1, wherein the extracting of the feature map comprises transforming the received input CXR image to a normalized image and then extracting the feature map from the normalized image using the neural network.

3. The method of claim 2, wherein the extracting of the feature map comprises transforming the input CXR image to the normalized image by normalizing a width, height, and pixel value range of the input CXR image to a predetermined range.

4. The method of claim 1, wherein the extracting of the feature map comprises extracting, from the input CXR image, the feature map that includes low level features of pneumonia, consolidation, lung opacity, pleural effusion, cardiomegaly, edema, atelectasis, pneumothorax, a support device, and no finding.

5. The method of claim 1, wherein the classifying of the lesion comprises classifying the lesion by combining information included in the feature map and estimating a final diagnosis using classification results of the classified lesion.

6. The method of claim 1, wherein the quantifying comprises generating a lesion probability map based on the extracted feature map and the classified lesion and quantifying severity of the input CXR image using the generated lesion probability map.

7. The method of claim 6, wherein the quantifying comprises segmenting each of a left lung field and a right lung field of the input CXR image into three areas, assigning a maximum lesion probabilistic value to each of the segmented areas, and quantifying the severity of the input CXR image with respect to each of the segmented areas using the assigned maximum lesion probabilistic value.

8. The method of claim 1, wherein the neural network is pretrained by a large-scale labeled first training dataset and then trained by supervised and weakly supervised learning with the vision transformer through training a small-scale labeled second training dataset with respect to the lesion to be classified.

9. A method of quantifying severity of infectious disease based on a vision transformer, the method comprising:
    transforming an input chest X-ray (CXR) image to a normalized image;
    extracting a feature map from the transformed normalized image using a pretrained neural network;
    classifying a lesion in the input CXR image using the vision transformer based on the extracted feature map; and
    quantifying severity of the input CXR image based on the extracted feature map and the classified lesion,
    wherein the quantifying comprises quantifying the severity of the input CXR image based on a combination of information included in the extracted feature map and the classified lesion and localizing a position of the lesion.

10. An apparatus for quantifying severity of infectious disease based on a vision transformer, the apparatus comprising:
    a receiver configured to receive an input chest X-ray (CXR) image;
    an extractor configured to extract a feature map from the received input CXR image using a pretrained neural network;
    a classifier configured to classify a lesion in the input CXR image using the vision transformer based on the extracted feature map; and
    a quantifier configured to quantify severity of the input CXR image based on the extracted feature map and the classified lesion,
    wherein the quantifier is configured to quantify the severity of the input CXR image based on a combination of information included in the extracted feature map and the classified lesion and to localize a position of the lesion.

11. The apparatus of claim 10, wherein the extractor is configured to transform the received input CXR image to a normalized image and then extract the feature map from the normalized image using the neural network.

12. The apparatus of claim 11, wherein the extractor is configured to transform the input CXR image to the normalized image by normalizing a width, height, and pixel value range of the input CXR image to a predetermined range.

13. The apparatus of claim 10, wherein the extractor is configured to extract, from the input CXR image, the feature map that includes low level features of pneumonia, consolidation, lung opacity, pleural effusion, cardiomegaly, edema, atelectasis, pneumothorax, a support device, and no finding.

14. The apparatus of claim 10, wherein the classifier is configured to classify the lesion by combining information included in the feature map and to estimate a final diagnosis using classification results of the classified lesion.

15. The apparatus of claim 10, wherein the quantifier is configured to generate a lesion probability map based on the extracted feature map and the classified lesion and to quantify severity of the input CXR image using the generated lesion probability map.

16. The apparatus of claim 15, wherein the quantifier is configured to segment each of a left lung field and a right lung field of the input CXR image into three areas, to assign a maximum lesion probabilistic value to each of the segmented areas, and to quantify the severity of the input CXR image with respect to each of the segmented areas using the assigned maximum lesion probabilistic value.

\* \* \* \* \*